(12) United States Patent
Rudorfer et al.

(10) Patent No.: US 11,742,079 B2
(45) Date of Patent: *Aug. 29, 2023

(54) METHODS AND APPARATUS FOR TROUBLESHOOTING INSTRUMENT MALFUNCTIONS

(71) Applicant: Siemens Healthcare Diagnostics Inc., Tarrytown, NY (US)

(72) Inventors: Arnold Rudorfer, Princeton, NJ (US); Steven Magowan, Elkton, MD (US); Joel Cambron, Briarcliff Manor, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 780 days.

This patent is subject to a terminal disclaimer.

(21) Appl. No.: 16/316,202

(22) PCT Filed: Jul. 24, 2017

(86) PCT No.: PCT/US2017/043434
§ 371 (c)(1),
(2) Date: Jan. 8, 2019

(87) PCT Pub. No.: WO2018/022474
PCT Pub. Date: Feb. 1, 2018

(65) Prior Publication Data
US 2021/0287789 A1    Sep. 16, 2021

Related U.S. Application Data

(60) Provisional application No. 62/366,343, filed on Jul. 25, 2016.

(51) Int. Cl.
*G06F 16/907* (2019.01)
*G16H 40/60* (2018.01)
(Continued)

(52) U.S. Cl.
CPC ......... *G16H 40/60* (2018.01); *G06F 11/0793* (2013.01); *G06F 16/907* (2019.01);
(Continued)

(58) Field of Classification Search
CPC ................................. G06Q 10/20; H04N 7/14
See application file for complete search history.

(56) References Cited

U.S. PATENT DOCUMENTS 5,778,381 A    7/1998  Sandifer
6,029,258 A    2/2000  Ahmad
(Continued)

FOREIGN PATENT DOCUMENTS

WO    WO-2015023443 A1 *    2/2015    ............ G06Q 10/20

OTHER PUBLICATIONS

International Search Report for PCT/US2017/043434, dated Oct. 12, 2017.

*Primary Examiner* — Reginald R Reyes

(57) ABSTRACT

Methods of troubleshooting non-event malfunctions. The methods include providing a database including pre-populated non-event issues and associated corrective actions, inputting search criteria regarding a particular non-event issue via entry of a search string at the user interface, parsing and normalizing the search string into a meta-data schema to produce a normalized search string, searching the database with the normalized search string to generate a listing of one or more particular corrective actions, and receiving the listing of one or more particular corrective actions that are associated with the normalized search string. Apparatus configured to carry out the methods are provided, as are other aspects.

11 Claims, 4 Drawing Sheets

(51) Int. Cl.
*G06F 16/903* (2019.01)
*G06F 11/07* (2006.01)
*G06N 5/02* (2023.01)
*G06N 5/01* (2023.01)

(52) U.S. Cl.
CPC ......... *G06F 16/90344* (2019.01); *G06N 5/01* (2023.01); *G06N 5/02* (2013.01)

(56) References Cited

U.S. PATENT DOCUMENTS

| | | |
|---|---|---|
| 6,694,314 B1 | 2/2004 | Sullivan et al. |
| 8,620,909 B1* | 12/2013 | Rennison ............ G06F 16/3332 707/723 |
| 10,643,747 B2 | 5/2020 | Rudorfer et al. |
| 2008/0016385 A1 | 1/2008 | Hollingsworth et al. |
| 2008/0172574 A1 | 7/2008 | Fisher |
| 2008/0294423 A1 | 11/2008 | Castellani et al. |
| 2016/0132375 A1* | 5/2016 | Jacobs .................. G16H 40/40 714/47.2 |
| 2017/0017538 A1 | 1/2017 | Rudorfer et al. |
| 2018/0149557 A1* | 5/2018 | Ishihara ................ G06Q 10/20 |
| 2019/0179855 A1* | 6/2019 | Hu ........................ G06F 40/232 |

\* cited by examiner

METHODS AND APPARATUS FOR TROUBLESHOOTING INSTRUMENT MALFUNCTIONS

RELATED APPLICATION

This application claims priority to U.S. Provisional Application Ser. No. 62/366,343 entitled "METHODS AND APPARATUS FOR TROUBLESHOOTING INSTRUMENT MALFUNCTIONS" filed on Jul. 25, 2016, the disclosure of which is hereby incorporated by reference in its entirety herein.

FIELD

The present disclosure relates to methods and apparatus adapted to rapidly resolve instrument malfunctions, and in particular malfunctions in automated biological liquid testing and processing instruments.

BACKGROUND

In biological liquid testing and processing, automated apparatus including the use of robotics may be used to process biological liquids (otherwise referred to herein as "specimens"). Such automated apparatus are complex and from time-to-time may experience various malfunctions. Certain types of recurring malfunctions are relative easy to diagnose as the apparatus themselves may generate an "error code," which leads the user to a set of instructions that provides a detailed solution to aid in rectifying the particular error-code-based malfunction. Other highly-complex malfunctions, which do not have an associated error code (hereinafter non-event malfunctions), may be multifactorial and much more difficult to diagnose and to solve.

Accordingly, methods and apparatus that may improve the speed and/or quality of non-event based malfunction diagnosis and solution in biological fluid testing and processing apparatus are sought after.

SUMMARY

In one method embodiment, a method of troubleshooting malfunctions of an instrument is provided. The method includes providing a database including a plurality of pre-populated non-event issues and associated corrective actions, inputting, via a user interface of the instrument, one or more search criteria regarding a particular non-event issue of the instrument, via entry of a search string at the user interface, parsing and normalizing the search string into a meta-data schema to produce a normalized search string; searching the database with the normalized search string to generate a listing of one or more particular corrective actions, and receiving at the user interface, the listing of one or more particular corrective actions that are associated with the normalized search string.

In an apparatus embodiment, an instrument malfunction troubleshooting apparatus is provided. The instrument malfunction troubleshooting apparatus includes a local instrument database stored on a local memory containing searchable data on non-event malfunction issues and associated corrective actions, an instrument user interface operatively configured to allow input of a search string concerning a particular non-event malfunction issue and output a particular corrective action, and a preprocessing application stored in the local memory and configured and operable to preprocess the search string into a metadata schema to produce a normalized search string.

In another method embodiment, a method of troubleshooting a malfunction of an instrument is provided. The method includes providing a database including a plurality of pre-populated non-event issues and associated corrective actions, inputting, via a user interface of the instrument, search criteria regarding a particular non-event issue of the instrument, via either an entry of a search string at a search box of an intelligent service assistant search screen or selection from a decision tree selection menu of the intelligent service assistant search screen which contains both the search box and selection menu: if an entry in the search box, parsing and normalizing the search string into a meta-data schema to produce a normalized search string, if the particular non-event issue is populated item in the decision tree selection menu, selecting the populated item, and searching the database with the normalized search string or populated item to generate a listing of one or more particular corrective actions, and receiving at the user interface, the listing of one or more particular corrective actions.

Still other aspects, features, and advantages of the present disclosure may be readily apparent from the following detailed description illustrating a number of example embodiments. The present invention may also be capable of different embodiments, and its several details may be modified in various respects, all without departing from the scope of the present disclosure. Accordingly, the disclosure is to cover all modifications, equivalents, and alternatives falling within the scope of the disclosure as defined in the appended claims.

DETAILED DESCRIPTION

In automated testing and processing apparatus (hereinafter referred to as "instruments"), malfunctions are typically diagnosed either by the apparatus-generated "error code," or in cases where no error code is generated (i.e., a non-event malfunction) by use of the knowledge of the operator, trial and error, by referring to an operator's manual, or by contacting a manufacturer's representative.

In particular, non-event malfunctions may be complex, very difficult to diagnose, multi-factorial, and may result in substantial instrument downtime because of the difficulty in proper diagnosis thereof. Thus, rapid resolution of such non-event malfunctions is problem that is in need of a solution.

In view of the foregoing, one or more embodiments of the disclosure provide methods and apparatus configured and operable to rapidly troubleshoot such non-event malfunctions. In one embodiment, a method includes providing a database including a plurality of pre-populated non-event issues and associated corrective actions, inputting, via entry of a search string at a user interface of the instrument, one or more search criteria regarding a particular non-event issue. The search string is parsed and normalized into a meta-data schema to produce a normalized search string. The database is searched with the normalized search string to generate a listing of one or more particular corrective actions for the non-event issue. The listing of one or more particular corrective actions that are associated with the normalized search string are received and outputted at the user interface. Apparatus embodiments for carrying out the method are also provided.

These and other aspects and features of embodiments of the disclosure will be described with reference to FIGS. 1-6 herein.

Figure 1:
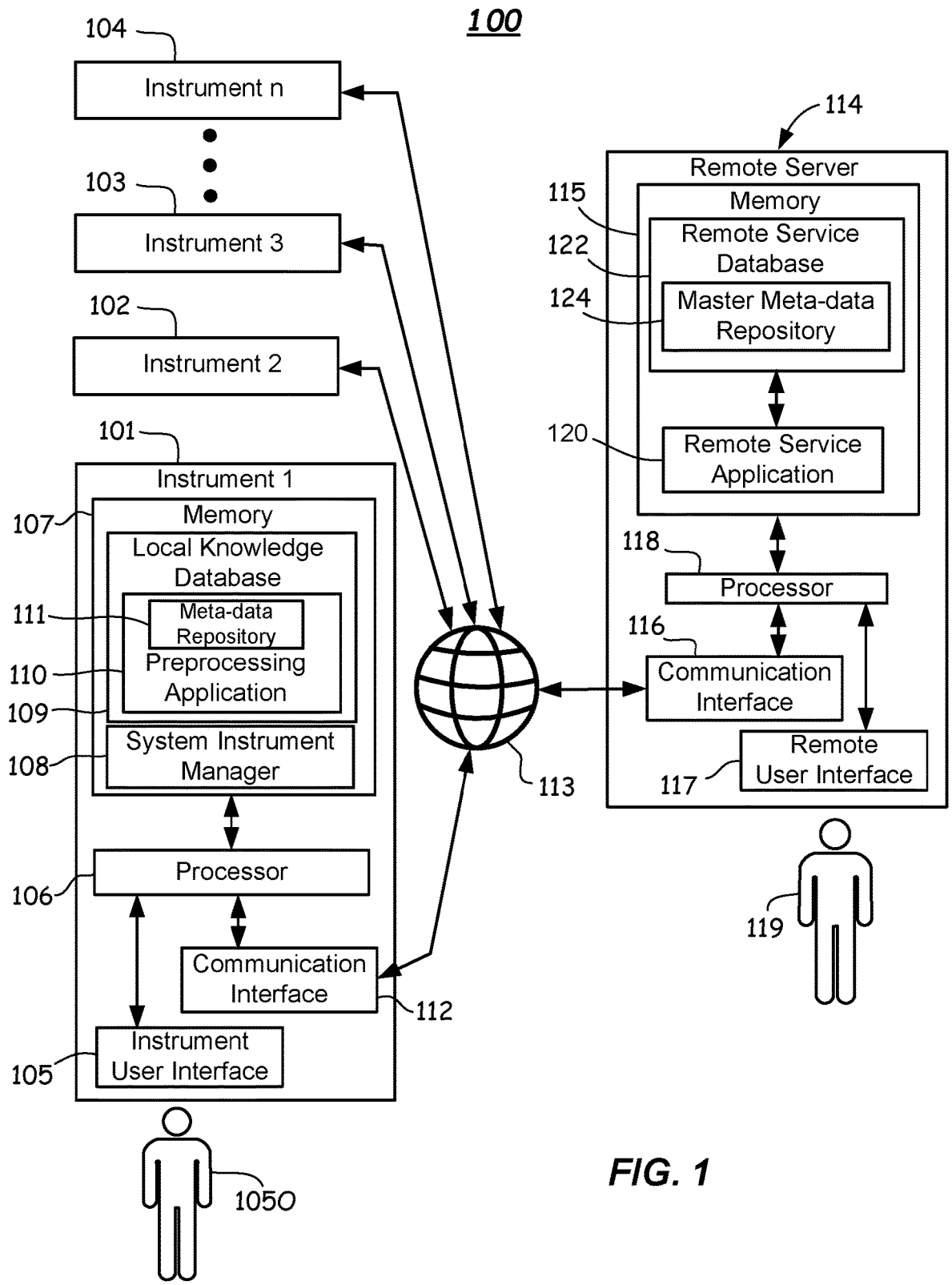
FIG. 1 illustrates a schematic diagram of an instrument malfunction troubleshooting apparatus for non-event based malfunction diagnosis according to one or more embodiments.

In accordance with one or more apparatus embodiments, referring to FIG. 1, an instrument malfunction troubleshooting apparatus 100 is shown and described. The instrument malfunction troubleshooting apparatus 100 may be used in any biological fluid testing instrument or device, such as an automated clinical analyzer, assaying instrument, or other processing device where specimen containers containing bio-fluid specimen are tested and/or processed. The instrument malfunction troubleshooting apparatus 100 includes an instrument 101 including an instrument user interface 105 (e.g., display monitor, keyboard and/or mouse, and possibly a printer), a processor 106, and memory 107. The instrument user interface 105 (e.g., display, keyboard and/or mouse), processor 106, and memory 107 may be provided as a workstation server computer that is coupled to the mechanical and electrical components of the instrument 101.

The instrument malfunction troubleshooting apparatus 100 may include a local knowledge database 109 stored in the memory 107 that contains searchable data on non-event malfunction issues and associated corrective actions. The instrument user interface 105 is operatively configured to allow input of a search string in a search string box wherein the search string is concerning a particular non-event malfunction issue. A corrective action instruction may be output by the instrument user interface 105 (e.g., displayed on the display monitor or provided as a printed report) so that the instrument operator 105O can correct the non-event malfunction issue.

The instrument malfunction troubleshooting apparatus 100 may include a preprocessing application 110 stored in the memory 107, which is configured and operable to preprocess the entered search string into a metadata schema to produce a normalized search string. The preprocessing application 110 comprises a software application that first parses the search string and then normalizes the remaining search terms into a normalized search string. The normalized search string is then compared to known pre-populated search terms stored in a meta-data repository 111 stored in the local knowledge database 109.

The memory 107 may include a system instrument manager 108, which may be embodied as a software application that facilitates data input and retrieval. The instrument 101 includes a communication interface 112 enabling communication with the internet 113 and with a remote server 114 located at a location remote from the instrument 101. For example, the remote server 114 may be positioned at a location of a manufacturer of the instrument 101, while the instrument 101 may be located at a lab location of a customer of the manufacturer. Other instruments 102, 103, 104, which may be the same as instrument 101, may also be in communication with the remote server 114 through the internet 113.

Remote server 114 may include memory 115, processor 118, communication interface 116, and remote user interface 117. Communication interface 116 may allow communication with the various instruments 101-104 such that software updates may be periodically provided thereto, as well as other data exchange. Software updates may include versions of software with updates of meta-data schema based upon input on search strings that have been used by the various instrument operators 105O. A master meta-data repository 124 may be included in the remote service database 122 and may include raw search terms used, associated synonyms, normalized search strings and associated non-event issues and corrective actions. The normalized search strings are correlated/paired with corrective actions that are stored in the remote service database 122. New software versions including revised search criteria and correlations to controlled vocabulary may be provided by pushing the software updates by action of the service operator 119. A remote service application 120, embodied as a software application, may operate to extract and store data from and to the remote service database 122.

Figure 5:
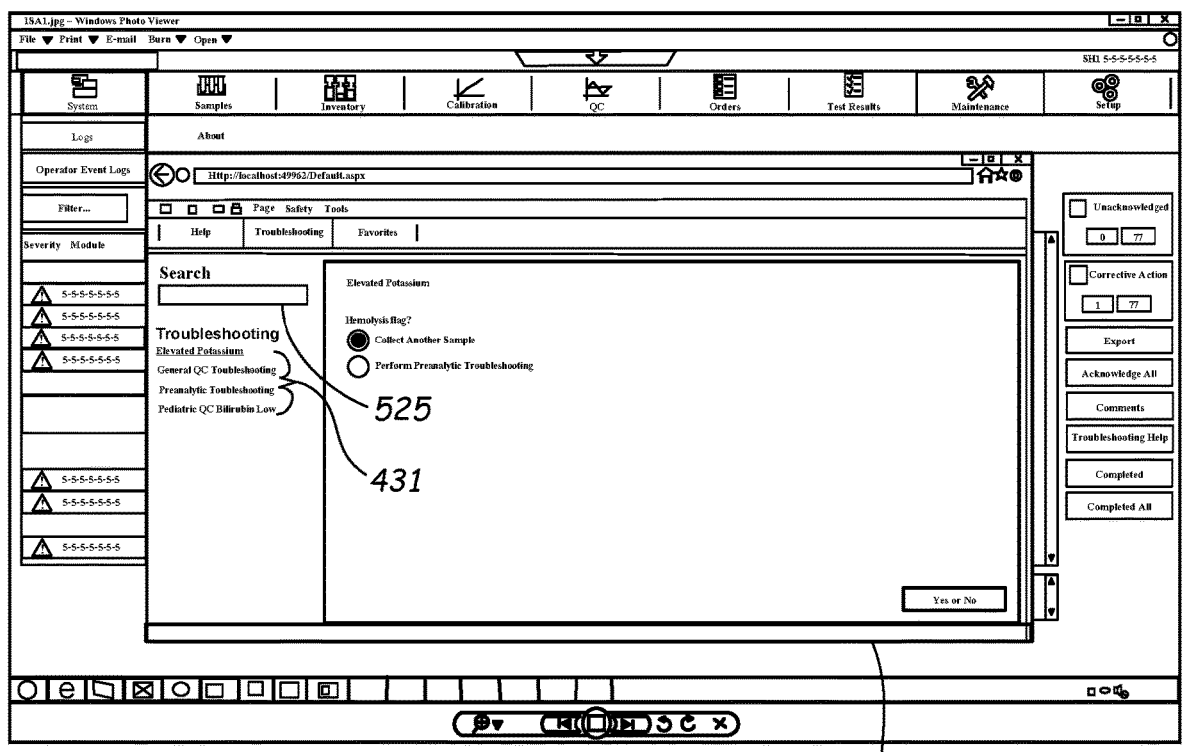
FIG. 5 illustrates a screen showing a search box and a decision tree selection menu according to one or more embodiments.

As can be seen from FIGS. 1 and 5, the system instrument manager 108 of each instrument 101-104 may provide the search strings inputted by instrument operator 105O into a search box 525 of an intelligent service assistant search screen 526 (see FIG. 5) of the instrument user interface 105 to the preprocessing application 110.

Figure 2:
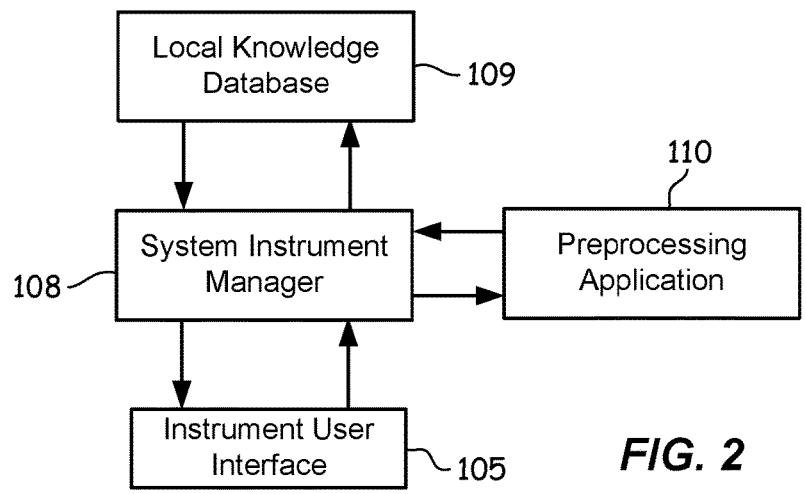
FIG. 2 illustrates a functional diagram showing the communication between components of the instrument malfunction troubleshooting apparatus for non-event based malfunction diagnosis according to one or more embodiments.
Figure 3:
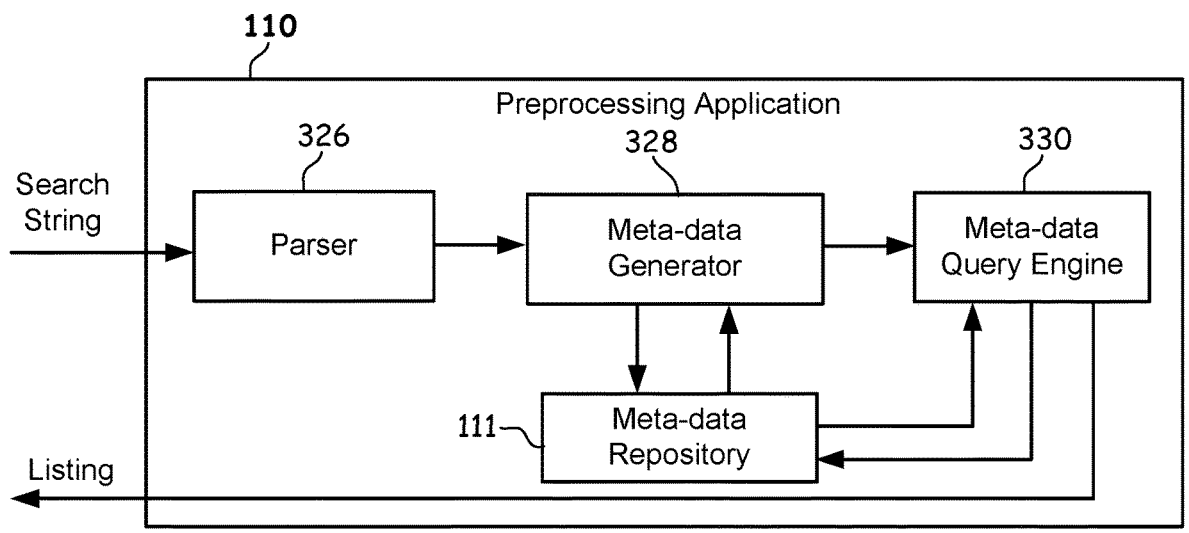
FIG. 3 illustrates a schematic diagram showing the communication between the functional components of the preprocessing application configured to preprocess inputted search strings according to meta-data schema according to one or more embodiments.

As shown in FIGS. 2 and 3, the parsing is carried out by the preprocessing application 110. A parser 326 of the preprocessing application 110 operates to separate the entered search string as entered into a search box 525 into parts and then data clean the search string by removing non-essential words therefrom for subsequent processing. Parsing may include subject, verb, and object determination. Parsing involves removing non-essential terms from the search string, such as the words: the, and, as, a, it, such, and the like. Any suitable parsing software may be used. Once parsed, the parsed terms are fed to a meta-data generator 328.

The meta-data generator 328 operates on the parsed search string to produce a normalized search string. The normalized search string and terms may also be stored in memory in the meta-data repository 111. The normalized search string may be generated in a controlled format, wherein the terms of the normalized search string may include synonyms of the various terms in the parsed search string. The normalized search string is then compared to known meta-data terms and strings also stored in the meta-data repository 111. Comparison is carried out by a meta-data query engine 330. If there is a match, then the meta-data query engine 330 may return a listing of one or more corrective actions. The listing of corrective actions may be provided to the instrument user interface 105. Feedback regarding a success of the one or more particular corrective actions may be provided to the remote server 114 that is configured to communicate with multiple instruments, including the instrument 101.

Figure 4:
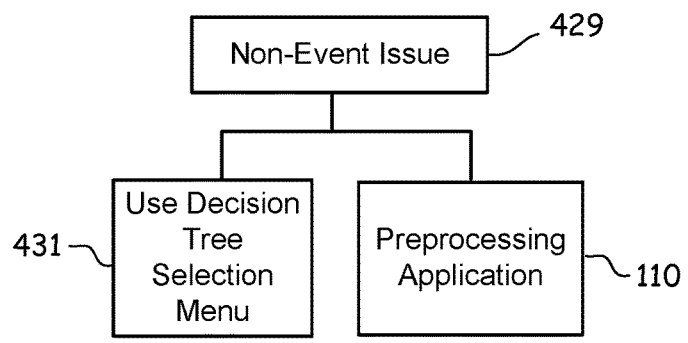
FIG. 4 illustrates a schematic diagram showing alternate input methods according to one or more embodiments.

FIG. 4 illustrates another embodiment wherein the non-event issue 429 is either input through use of a preprocessing application 110 and input of a search string in a search box 525 (FIG. 5), or optionally by the use of a decision tree selection menu 431. Decision tree selection menu 431 (see also FIG. 5) may be a drop down menu or selectable list of prepopulated non-event issues on the intelligent service assistant search screen 526 that have resulted from previous meta-data searches, for example. Selection of one from the prepopulated list will display a screen of one or more potential corrective actions. Thus, in the present embodiment, the most common non-event issues 429 may be configured and presented as menu items as a decision tree selection menu 431 and other non-event issues 429 may be searchable via entry in the search box 525 through use of the preprocessing application 110.

Figure 6:
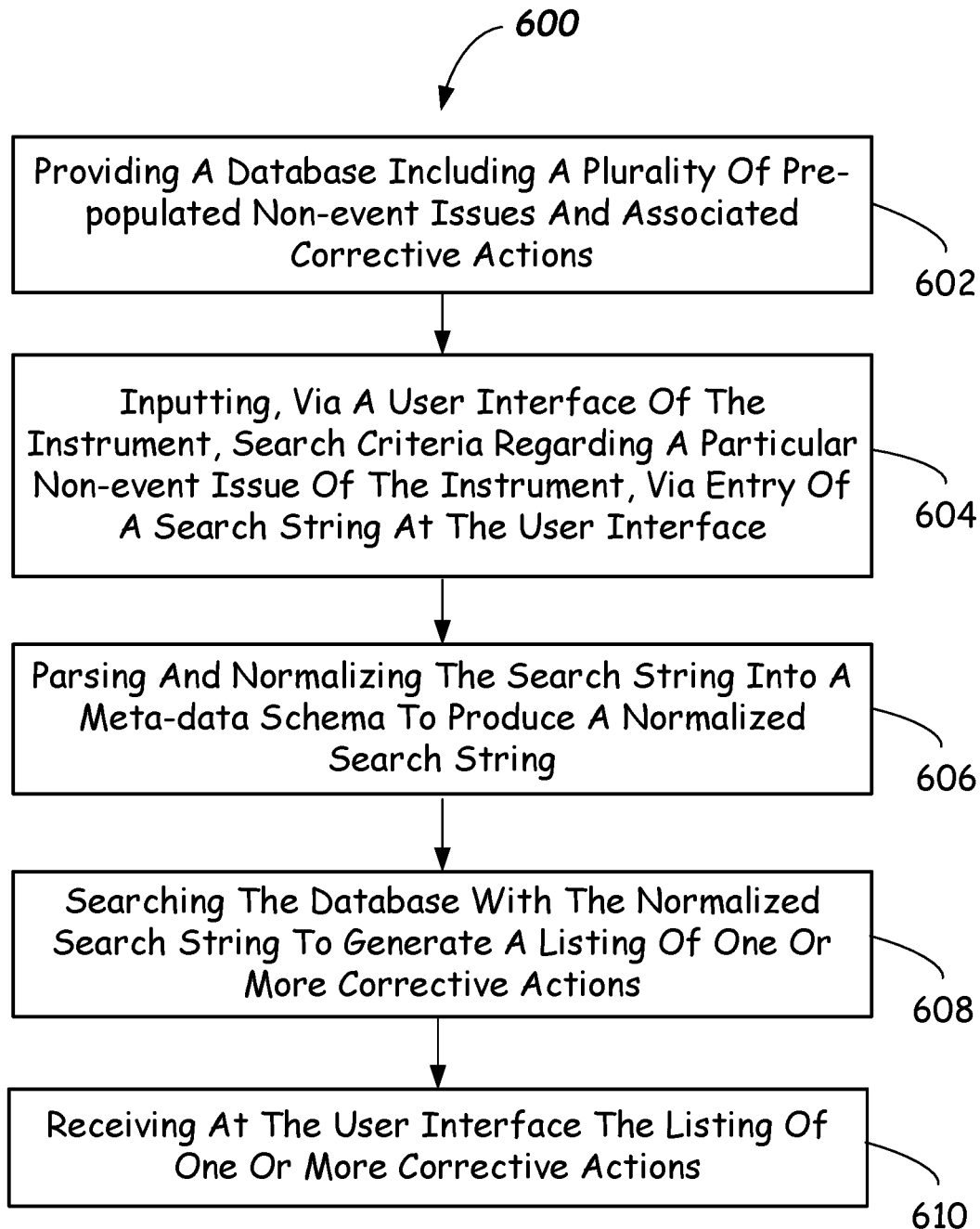
FIG. 6 illustrates a flowchart of a method of troubleshooting a malfunction of an instrument according to one or more embodiments.

In accordance with another embodiment of the disclosure shown and described in FIG. 6, a method of troubleshooting malfunctions of an instrument (e.g., instruments 101, 102, 103, . . . , and/or 104) is provided. The method 600 includes, in 602, providing a database (e.g., local knowledge database 109 including meta-data repository 111) including a plurality of pre-populated non-event issues and associated corrective actions. The non-event issues may relate to: a test result was not generated, a calibration that is out of specification, and a control that is out of specification, for example. Other non-event issues may be correlated. The issues may be correlated to specific tests, such as clinical chemistry, colorimetric, turbidimetric, enzymatic, immunoassay, or drug testing. Other specific tests may benefit as well.

The method 600 includes, in 604, inputting, via a user interface (e.g., instrument user interface 105) of the instrument (e.g., instrument 101, 102, 103, . . . , and/or 104), search criteria regarding a particular non-event issue of the instrument, via entry of a search string at the user interface (e.g., instrument user interface 105). Search strings may be, for example: received no test result, calibrator is out of specification, quality control test is out of spec, result seems high, and the like. In some embodiments, the issue type, instrument component, and/or usage category may be pre-selected to narrow the range/scope of the search.

In 606, the search string is parsed and normalized into a meta-data schema to produce a normalized search string. The meta-data repository 111 includes the meta-data schema, which is compared to the normalized search string. In 608, the database (e.g., the meta-data repository 111) is searched with the normalized search string to generate a listing of one or more particular corrective actions. Searching may be carried out by the meta-data query engine (e.g., meta-data query engine 330). In 610, the listing of one or more particular corrective actions that are associated with the normalized search string may be receiving at the user interface (e.g., user interface 105). The listing may be displayed on a display monitor or printed as a hard copy. Once the instrument operator 105O has used the corrective action to solve the non-event issue, the instrument operator 105O may be given an opportunity, through suitable questions of the instrument user interface 105 to provide feedback on the success of the corrective action. This success feedback data may be transmitted over the internet 113 to the remote server 114 and stored in the master meta-data repository 124.

While specific apparatus, system, and methods have been shown by way of example embodiments herein, it should be understood that other and different embodiments are possible. It is intended that the disclosure is to cover all modifications, equivalents, and alternatives falling within the scope of the appended claims.

What is claimed is:

1. A method of troubleshooting malfunctions of a biological fluid testing device, the method performed by an instrument comprising a processor and a memory, the method comprising:
   providing a database stored in the memory, the database including a plurality of pre-populated non-event issues and associated corrective actions for which the biological fluid testing device does not generate an error code;
   receiving, via a user interface of the instrument, search criteria regarding a particular non-event issue of the instrument, via entry of a search string at the user interface;
   parsing and normalizing the search string into a meta-data schema to produce a normalized search string that includes one or more synonyms of one or more terms in the search string;
   searching the database with the normalized search string to generate a listing of one or more particular corrective actions in response to correlating the normalized search string with a pre-populated non-event issue;
   outputting, via the user interface, the listing of one or more particular corrective actions that are associated with the normalized search string;
   requesting feedback, via the user interface, after implementation of the one or more particular corrective actions by a user regarding whether the one or more particular corrective actions were successful;
   communicating at least the search string, the normalized search string, and the feedback to a remote server configured to communicate with the instrument and multiple other instruments to update respective databases of the instrument and the multiple other instruments; and
   providing, from the remote server, software updates to the respective databases based on the feedback and including revised search criteria and correlations to controlled vocabulary and updated meta-data schema based on received search strings, the remote server comprising a master repository that includes raw search terms used, associated synonyms, normalized search strings, and associated non-event issues and corrective actions.

2. The method of claim 1, wherein the one or more search criteria comprise one of:
   a test result was not generated;
   a calibration that is out of specification; and
   a control that is out of specification.

3. The method of claim 1, comprising saving the normalized search string in a meta-data repository.

4. The method of claim 3, wherein the meta-data repository is located in a local database of the instrument.

5. The method of claim 3, comprising retrieving a listing of one or more particular corrective actions from the meta-data repository using a meta-data query engine.

6. The method of claim 1, comprising communicating the normalized search string to a remote database.

7. The method of claim 1, wherein the plurality of pre-populated non-event issues comprises one selected from a group of:
   an issue with a specimen;
   an issue with a calibrator;
   an issue with a control; and
   an issue with a test result.

8. The method of claim 1, wherein the instrument further comprises a preprocessing application and a system instrument manager stored in the memory.

9. The method of claim 1, wherein parsing comprises reducing the search string by removing non-essential terms to form a parsed search screen.

10. The method of claim 9, wherein normalizing comprises comparing the parsed search string to pre-populated search terms stored in the database.

11. The method of claim 10, wherein the pre-populated search terms stored in the database are updated with parsed search terms to improve search capability.

* * * * *